United States Patent [19]

Stetter et al.

[11] 4,316,910
[45] Feb. 23, 1982

[54] COMBATING ARTHROPODS WITH SUBSTITUTED 2-CARBAMOYLOXIMINO-BUTANES

[75] Inventors: Jörg Stetter, Wuppertal; Bernhard Homeyer, Leverkusen; Ingeborg Hammann, Cologne; Hans-Ludwig Elbe, Wuppertal, all of Fed. Rep. of Germany

[73] Assignee: Bayer Aktiengesellschaft, Leverkusen, Fed. Rep. of Germany

[21] Appl. No.: 176,814

[22] Filed: Aug. 11, 1980

[30] Foreign Application Priority Data

Aug. 18, 1979 [DE] Fed. Rep. of Germany ....... 2933600

[51] Int. Cl.$^3$ .................. A01N 47/12; C07C 149/437
[52] U.S. Cl. ............................ 424/298; 260/453 RW; 424/300; 424/327; 560/148; 564/91; 564/101; 564/102; 564/255
[58] Field of Search ................ 564/255, 91, 101, 102; 424/327, 298, 300; 560/148; 260/453 RW

[56] References Cited
U.S. PATENT DOCUMENTS 3,875,232  4/1975  Magee .................................. 564/255
3,901,683  11/1975  Limpel et al. ......................... 71/98
3,937,738  4/1974  Throckmorton ................... 564/255

Primary Examiner—Natalie Trousof

Assistant Examiner—L. Hendriksen
Attorney, Agent, or Firm—Sprung, Felfe, Horn, Lynch & Kramer

[57] ABSTRACT

Substituted 2-carbamoyloximino-butanes of the formula

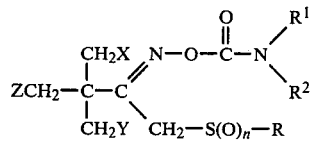

in which
R is alkyl or alkylthioalkyl,
$R^1$ is alkyl, alkoxyalkyl, alkenyl or alkynyl,
$R^2$ is hydrogen, alkyl or $-SR^3$,
$R^3$ is alkyl, halogenoalkyl, optionally substituted phenyl, alkoxycarbonyl, $-N(CH_3)R^4$, or a radical identical to that to which $-SR^3$ is bonded,
$R^4$ is alkyl, alkoxycarbonyl or optionally substituted phenylsulphonyl,
X is hydrogen or halogen,
Y is hydrogen or halogen,
Z is halogen, and
n is 0, 1 or 2, which possess arthropodicidal activity.

8 Claims, No Drawings

COMBATING ARTHROPODS WITH SUBSTITUTED 2-CARBAMOYLOXIMINO-BUTANES

The present invention relates to certain new substituted 2-carbamoyl-oximino-butanes, to a process for their preparation and to their use as agents for combating pests.

It has already been disclosed that oxime-carbamates, for example 1-cyano-2-methylpropanaldoxime-N-methylcarbamate and 1-cyano-butanaldoxime-N-methylcarbamate or 3,3-dimethyl-2-methylcarbamoyloximino-1-methylthiobutane (decamox) or N,N-dimethyl-α-methylcarbamyloximino-α-methylthio-acetamide (oxamyl) have pesticidal properties (see German Published Specification DE-OS No. 1,567,142, DE-OS (German Published Specification) No. 2,216,838 and U.S. Pat. Nos. 3,530,220 and 3,658,870). However, their action is not always completely satisfactory, especially when small amounts are applied.

The present invention now provides, as new compounds, the substituted 2-carbamoyloximino-butanes of the general formula

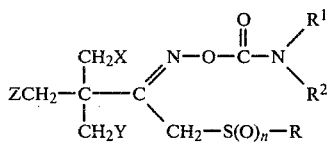

in which
R represents alkyl or alkylthioalkyl,
$R^1$ represents alkyl, alkoxyalkyl, alkenyl or alkynyl,
$R^2$ represents hydrogen, alkyl or the group $-SR^3$,
$R^3$ represents alkyl, halogenoalkyl, optionally substituted phenyl, alkoxycarbonyl, the grouping $-N(CH_3)R^4$ or a radical identical to that to which the group $-SR^3$ is bonded,
$R^4$ represents alkyl, alkoxycarbonyl or optionally substituted phenylsulphonyl,
X represents hydrogen or halogen,
Y represents hydrogen or halogen,
Z represents halogen and
n represents 0, 1 or 2.

The compounds of the formula (I) can exist in the syn-form or anti-form; they are predominantly obtained as mixtures of the two forms.

The invention also provides a process for the preparation of a substituted 2-carbamoyloximino-butane of the formula (I) in which an oxime of the general formula

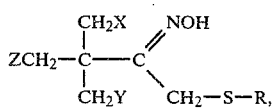

in which R, X, Y and Z have the meanings indicated above,
(a) is reacted with an isocyanate of the general formula $$R^1-N=C=O \quad (III),$$

in which $R^1$ has the meaning indicated above,
in the presence of a diluent and if appropriate in the presence of a catalyst, or (b) is reacted with a carbamoyl halide of the general formula

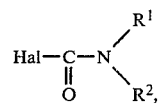

in which
$R^1$ and $R^2$ have the meanings indicated above and
Hal represents fluorine, chlorine or bromine,
in the presence of a diluent and of an acid-binding agent, or (c) a carbamoyloximino-butane, obtainable by process variant (a), or (b), of the general formula

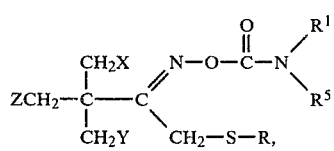

in which
R, $R^1$, X, Y and Z have the meanings indicated above and
$R^5$ represents hydrogen or alkyl with 1 to 4 carbon atoms,
is oxidized in a customary manner (a compound of the formula (I) in which n=1 or n=2 being obtained, depending on the oxidizing agent used), or (d) a carbamoyloximino-butane, obtainable by process variant (a) or (c), of the general formula

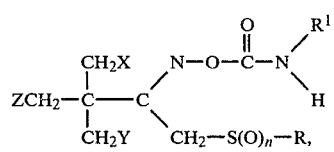

in which R, $R^1$, X, Y, Z and n have the meanings indicated above,
is reacted with a sulphenyl chloride or bromide of the general formula $$Hal'-S-R^3 \quad (VI),$$

in which
$R^3$ has the meaning indicated above and
Hal' represents chlorine or bromine,
in the presence of a diluent and of an acid-binding agent.

The new substituted 2-carbamoyloximino-butanes of the formula (I) are suitable for combating pests. They have powerful insecticidal and acaricidal properties, and in particular also root-systemic properties. Surprisingly, the compounds according to the invention exhibit a considerably more powerful action than the known oximecarbamates 1-cyano-2-methylpropanaldoxime-N-methylcarbamate, 1-cyano-butanaldoxime-N-methylcarbamate, 3,3-dimethyl-2-methylcarbamoyloximino-1-methylthio-butane and N,N-dimethyl-α-methylcarbamyloximino-α-methylthioacetamide, which are closely related compounds chemically and from the point of view of their action. The active compounds according to the invention thus represent an enrichment of the art.

The formula (I) provides a general definition of the substituted 2-carbamoyloximino-butanes according to the invention. Preferably, in this formula R represents straight-chain or branched alkyl with 1 to 4 carbon atoms or alkylthioalkyl with 1 to 4 carbon atoms in each alkyl part, $R^1$ represents straight-chain or branched alkyl with 1 to 4 carbon atoms, alkoxyalkyl with 1 to 4 carbon atoms in each alkyl part, or alkenyl or alkynyl with in either case 2 to 4 carbon atoms, $R^2$ represents hydrogen, alkyl with 1 to 4 carbon atoms or the group $-SR^3$, $R^3$ represents straight-chain or branched alkyl with 1 to 4 carbon atoms, halogenoalkyl with 1 to 2 carbon atoms and up to 5 halogen atoms (especially fluorine and chlorine atoms), optionally substituted phenyl [the or each substituent being selected from halogen (especially fluorine, chlorine or bromine), alkyl with 1 to 2 carbon atoms and halogenoalkyl with 1 to 2 carbon atoms and up to 5 halogen atoms (especially fluorine atoms and chlorine atoms)], alkoxycarbonyl with 1 to 4 carbon atoms in the alkyl part, the grouping $-N(CH_3)R^4$ or a radical identical to that to which the group $-SR^3$ is bonded, $R^4$ represents alkyl with 1 to 4 carbon atoms, alkoxycarbonyl with 1 to 4 carbon atoms in the alkyl part or phenylsulphonyl which is optionally substituted on the phenyl part [the or each substituent being selected from halogen (especially fluorine, chlorine or bromine), alkyl with 1 to 2 carbon atoms and halogenoalkyl with 1 to 2 carbon atoms and up to 5 halogen atoms (especially fluorine atoms and chlorine atoms)], X represents hydrogen, fluorine, chlorine or bromine, Y represents hydrogen, fluorine, chlorine or bromine, Z represents fluorine, chlorine, or bromine, and n represents 0, 1 or 2.

Very particularly preferred substituted 2-carbamoyloximino-butanes of the formula (I) are those in which R represents methyl, ethyl, methylthiomethyl or ethylthiomethyl; $R^1$ represents methyl, ethyl, methoxymethyl or allyl; $R^2$ represents hydrogen, methyl, ethyl or the group $-SR^3$; $R^3$ represents methyl, trifluoromethyl, chlorodifluoromethyl, dichlorofluoromethyl, trichloromethyl, phenyl which is optionally substituted by chlorine or by trifluoromethyl, methoxycarbonyl, ethoxycarbonyl or the grouping $-N(CH_3)R^4$, or $R^3$ represents a radical identical to that to which the group $-SR^3$ is bonded; $R^4$ represents methyl, ethyl, methoxycarbonyl, ethoxycarbonyl or phenylsulphonyl which is optionally substituted by chlorine or methyl; and X, Y, Z and the index n have the meanings indicated above.

The following compounds may be mentioned specifically, in addition to the compounds mentioned later in the preparative examples:

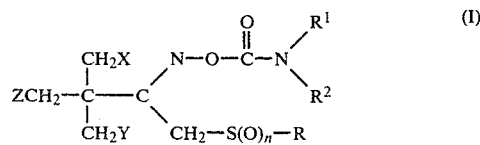

(I)

| X | Y | Z | R | $R^1$ | $R^2$ | n |
|---|---|---|---|---|---|---|
| H | H | F | $CH_3$ | $CH_3$ | $-SCH_3$ | 0 |
| H | H | Cl | $CH_3$ | $CH_3$ | $-SCH_3$ | 0 |
| H | H | Br | $CH_3$ | $CH_3$ | $-SCH_3$ | 0 |
| H | F | F | $CH_3$ | $CH_3$ | $-SCH_3$ | 0 |
| H | Cl | Cl | $CH_3$ | $CH_3$ | $-SCH_3$ | 0 |
| H | Br | Br | $CH_3$ | $CH_3$ | $-SCH_3$ | 0 |
| H | H | F | $CH_3$ | $CH_3$ | $-S-\text{C}_6\text{H}_4-Cl$ | 0 |
| H | H | Cl | $CH_3$ | $CH_3$ | $-S-\text{C}_6\text{H}_4-Cl$ | 0 |
| H | H | Br | $CH_3$ | $CH_3$ | $-S-\text{C}_6\text{H}_4-Cl$ | 0 |
| H | F | F | $CH_3$ | $CH_3$ | $-S-\text{C}_6\text{H}_4-Cl$ | 0 |
| H | Cl | Cl | $CH_3$ | $CH_3$ | $-S-\text{C}_6\text{H}_4-Cl$ | 0 |
| H | Br | Br | $CH_3$ | $CH_3$ | $-S-\text{C}_6\text{H}_4-Cl$ | 0 |
| H | H | F | $CH_3$ | $CH_3$ | $-S-CCl_3$ | 0 |
| H | H | Cl | $CH_3$ | $CH_3$ | $-S-CCl_3$ | 0 |
| H | H | Br | $CH_3$ | $CH_3$ | $-S-CCl_3$ | 0 |
| H | F | F | $CH_3$ | $CH_3$ | $-S-CCl_3$ | 0 |
| H | Cl | Cl | $CH_3$ | $CH_3$ | $-S-CCl_3$ | 0 |
| H | Br | Br | $CH_3$ | $CH_3$ | $-S-CCl_3$ | 0 |
| H | H | F | $CH_3$ | $CH_3$ | $-S-N(CH_3)-COOC_2H_5$ | 0 |
| H | H | Cl | $CH_3$ | $CH_3$ | $-S-N(CH_3)-COOC_2H_5$ | 0 |
| H | H | Br | $CH_3$ | $CH_3$ | $-S-N(CH_3)-COOC_2H_5$ | 0 |
| H | H | H | $CH_3$ | $CH_3$ | H | 0 |
| H | Cl | Cl | $CH_3$ | $CH_3$ | H | 0 |
| H | Br | Br | $CH_3$ | $CH_3$ | H | 0 |
| H | H | Cl | $CH_3$ | $CH_3$ | H | 0 |
| H | H | Br | $CH_3$ | $CH_3$ | H | 0 |
| H | H | F | $CH_3$ | $CH_3$ | H | 1 |
| H | F | F | $CH_3$ | $CH_3$ | H | 1 |
| H | H | F | $CH_3$ | $CH_3$ | H | 2 |
| H | F | F | $CH_3$ | $CH_3$ | H | 2 |
| F | F | F | $CH_3$ | $CH_3$ | H | 0 |
| F | F | F | $CH_3$ | $CH_3$ | H | 1 |
| F | F | F | $CH_3$ | $CH_3$ | H | 2 |
| H | H | F | $CH_3$ | $CH_3$ | $-S-N(CH_3)-SO_2-\text{C}_6\text{H}_4-CH_3$ | 0 |
| H | F | F | $CH_3$ | $CH_3$ | $-S-N(CH_3)-SO_2-\text{C}_6\text{H}_4-CH_3$ | 0 |
| H | H | F | $CH_3$ | $CH_3$ | $-S-N(CH_3)_2$ | 0 |
| H | F | F | $CH_3$ | $CH_3$ | $-S-N(CH_3)_2$ | 0 |
| H | F | F | $CH_3$ | $CH_3$ | dimer | 0 |

If, for example, 3,3-dimethyl-4-fluoro-1-methylthio-2-hydroximino-butane and methyl isocyanate are used as starting substances in process variant (a), the course of the reaction can be represented by the following equation:

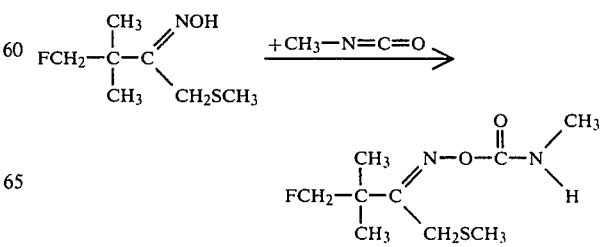

If, for example 3,3-dimethyl-4-fluoro-1-methylthio-2-hydroximino-butane and N-methyl-N-trichloromethyl-2-mercapto-carbamoyl fluoride are used as starting substances in process variant (b), the course of the reaction can be represented by the following equation:

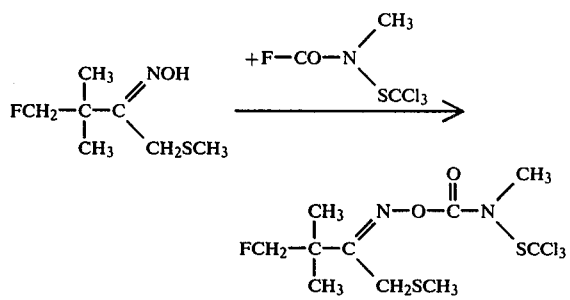

If, for example, 2 mols of 3,3-dimethyl-4-fluoro-1-methylthio-2-hydroximino-butane and 1 mol of N,N'-bis-(fluorocarbonyl)-thio-bis-methylamine are used as starting substances in process variant (b), the course of the reaction can be represented by the following equation:

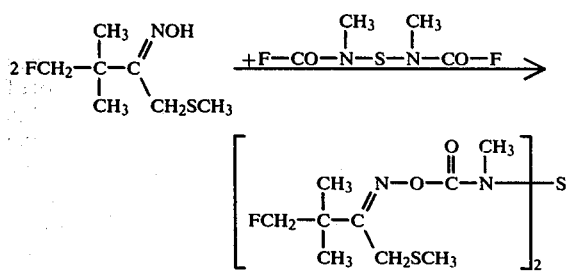

If, for example, 3,3-dimethyl-4-fluoro-2-methylcarbamoyl-oximino-1-methylthio-butane is used as the starting substance and hydrogen peroxide is used as the oxidising agent in process variant (c), the course of the reaction can be represented by the following equation:

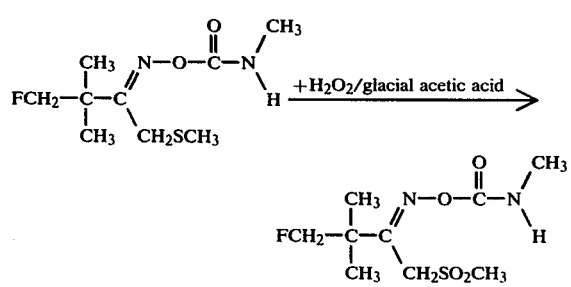

If, for example, 3,3-dimethyl-4-fluoro-2-methylcarbamoyl-oximino-1-methylthio-butane and 4-chlorophenylsulphenyl chloride are used as starting substances in process variant (d), the course of the reaction can be represented by the following equation:

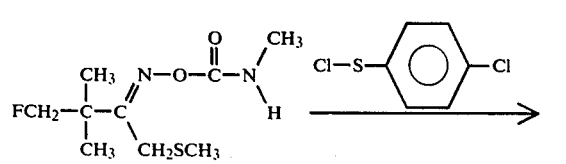

-continued

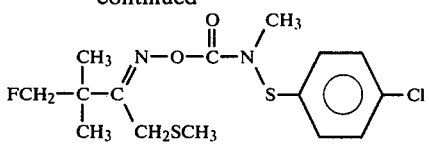

The formula (II) provides a general definition of the oximes to be used as starting substances for process variants (a) and (b). In this formula, R, X, Y, Z and n preferably have those meanings which have already been mentioned as preferred in the case of the compounds of the formula (I).

The oximes of the formula (II) have not hitherto been described in the literature. However, they can be obtained in a known manner, by reacting ketones of the general formula

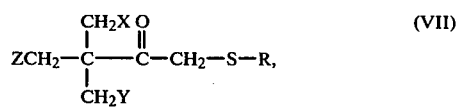

in which R, X, Y and Z have the meanings indicated above, with hydroxylamine in the presence of a solvent, preferably an alcohol or aqueous alcohol, at a temperature between 20° and 100° C., preferably between 50° and 80° C. The hydroxylamine is preferably employed in the form of one of its salts, in particular as the hydrochloride, in the presence of an acid-binding agent, for example sodium carbonate. The resultant compound of the formula (II) is isolated by a procedure in which the product formed during the reaction is worked up by customary methods, after distilling off the solvent (see also the preparative examples).

The ketones of the formula (VII) can be obtained by reacting α-halogeno-ketones of the general formula

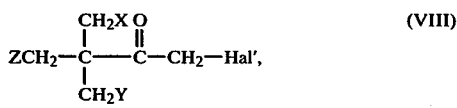

in which Hal', X, Y and Z have the meanings indicated above, with mercaptans of the general formula

in which R has the meaning indicated above, in the presence of an inert organic solvent, for example methanol, and in the presence of a base, for example sodium methylate, at a temperature between 0° and 100° C. (see also the preparative examples).

Some of the α-Halogeno-ketones of the formula (VIII) are known (see, for example, German Published Specification DE-OS No. 2,632,603 [Le A 17 273]), and are the subject of German patent application No. P 29 18 894 of 10.05.1979 [Le A 19 618]. They are obtained by adding chlorine or bromine to butane derivatives of the general formula

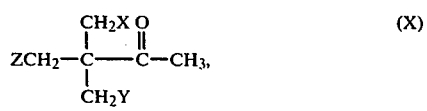

in which X, Y and Z have the meanings indicated above, in the presence of an inert organic solvent, for example ether or a chlorinated hydrocarbon, at room temperature (see also the preparative examples), or reacting the compounds of the formula (X) with customary chlorinating agents, for example sulphuryl chloride, at 20° to 60° C.

The formula (III) provides a general definition of the isocyanates also required as starting substances for process variant (a). In this formula, $R^1$ preferably has the meaning which has already been mentioned as preferred in the case of the compounds of the formula (I).

The isocyanates of the formula (III) are known, or they can be prepared by generally customary and known processes.

The formula (IV) provides a general definition of the carbamoyl halides also required as starting substances for process variant (b). In this formula, $R^1$ and $R^2$ preferably have those meanings which have already been mentioned as preferred in the case of the compounds of the formula (I).

Carbamoyl halides of the formula (IV) are known and can be prepared by generally customary and known processes, for example by reacting amines with phosgene (these processes are known from general textbooks of organic chemistry) or by reacting the corresponding carbamic acid halides with corresponding sulphenyl chlorides (in this context, see also the statements in German Published Specification DE-AS No. 1,297,095, German Published Specifications DE-OS Nos. 2,357,930 and 2,409,463, and U.S. Pat. No. 3,939,192).

The formula (VI) provides a general definition of the sulphenyl chlorides or bromides also required as starting substances for process variant (d). In this formula, $R^3$ preferably has those radicals which have already been mentioned as preferred in the case of the compounds of the formula (I).

The sulphenyl chlorides or bromides are generally known compounds of organic chemistry.

Preferred diluents for the reaction according to process variants (a), (b) and (d) are any of the inert organic solvents. These include, as preferences, ketones, such as diethyl ketone, and in particular acetone and methyl ethyl ketone; nitriles, such as propionitrile, and in particular acetonitrile; alcohols, such as ethanol or isopropanol; ethers, such as tetrahydrofuran or dioxane; formamides, such as, in particular, dimethylformamide; and halogenated hydrocarbons, such as methylene chloride, carbon tetrachloride or chloroform.

If the reaction according to process variants (b) and (d) is carried out in the presence of an acid-binding agent, it is possible to add any of the inorganic or organic acid-binding agents which can customarily be used, especially an alkali metal carbonate or bicarbonate, preferably sodium carbonate, potassium carbonate or sodium bicarbonate, or a lower tertiary alkylamine, cycloalkylamine or aralkylamine, for example triethylamine, N,N-dimethyl-benzylamine or dicyclohexylamine, or pyridine or diazabicyclooctane.

Preferred catalysts which can be used in process variant (a) are tertiary bases, such as triethylamine and pyridine, and organo-tin compounds, for example dibutyl-tin dilaurate.

The reaction temperatures can be varied within a substantial range in carrying out process variant (a). In general, the reaction is carried out between 0° and 100° C., preferably between 20° and 85° C.

In carrying out process variant (a), 1 to 2 mols of isocyanate of the formula (III) are employed per mol of the compound of the formula (II). To isolate the resultant compound of the formula (I), the solvent is distilled off and the residue is worked up by customary methods.

The reaction temperatures can be varied within a substantial range in carrying out process variant (b). In general, the reaction is carried out between 0° and 100° C., preferably between 10° and 80° C.

In carrying out process variant (b), 1 to 2 mols, or in the case of a dimeric product 0.5 mol, of carbamoyl halide of the formula (IV) and 1 to 2 mols of acid-binding agent are preferably employed per mol of the compound of the formula (II). The resultant compound of the formula (I) is isolated in a generally customary and known manner.

Possible oxidizing agents for process variant (c) are any of the inorganic and organic oxidizing agents which can customarily be used, such as chlorine in water; a peracid, for example meta-chloroperbenzoic acid; hydrogen peroxide in glacial acetic acid or methanol; potassium permanganate; or chromic acid.

The reaction temperatures can be varied within a substantial range in the oxidation according to process variant (c). In general, the reaction is carried out between −30° and +100° C., preferably at from −10° to +80° C.

In carrying out the oxidation according to process variant (c), 1 to 4 mols of oxidizing agent are employed per mol of the compound of the formula (V). If 1 mol of oxidizing agent, such as meta-chloroperbenzoic acid in methylene chloride or hydrogen peroxide in acetic anhydride, is used at a temperature between −10° and +10° C., the compounds of the formula (I) according to the invention in which n=1 are preferentially formed. In the case of an excess of oxidizing agent and higher temperatures (10° to 80° C.), the compounds of the formula (I) according to the invention in which n=2 are preferentially formed.

To isolate the oxidation product, either the reaction mixture is poured into ice-water and filtered and the precipitate which remains is washed and dried, if appropriate, or the reaction solution is adjusted to pH 7 to 8 and extracted with an organic solvent, then extracted with an organic solvent, the extracted phase is dried and the solvent is distilled off. In either case, the reaction product can be purified by recrystallization or column chromatography.

The reaction temperatures can be varied within a substantial range in carrying out process variant (d). In general, the reaction is carried out between 0° and 100° C., preferably between 10° and 50° C.

The starting substances are preferably employed in equimolar amounts in carrying out process variant (d). The resultant compound of the formula (I) is isolated by customary methods.

In some cases, it is also possible to carry out the individual stages of forming the precursors for the preparation of the oximes of the formula (II) and the reaction thereof to give the substances according to the invention in a so-called one-pot reaction, without isolating the particular intermediate products.

The active compounds are well tolerated by plants, have a favorable level of toxicity to warm-blooded animals, and can be used for combating arthropod pests, especially insects or acarids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Tricholusia ni, Carpocapsa pomonella,* Pieris spp., Chilo spp., *Pyrausta nubilalis, Ephestia keuhniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Cryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp. Tarsonemus spp., *Bryobia praetiosa,* Panonychus spp. and Tetranychus spp..

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylenefatty alcohol esters, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods or to a habitat thereof, a compound of the present invention alone or in the form of a composition containing as active ingredient a compound of the present invention in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

(Process variant a)

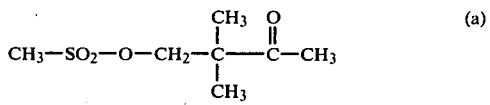

232 g (2 mols) of 3,3-dimethyl-4-hydroxy-2-butanone (for the preparation, see Beilstein H 1 E III 3,239, IV 4,030 and Bull. Soc. Chim. France 1964, 2,849) were reacted with 229 g (2 mols) of methanesulphonyl chloride in 700 ml of absolute pyridine at 0° to 5° C. After leaving the mixture to stand at 20° C. for 12 hours, it was diluted with methylene chloride and extracted by shaking with icewater. The organic phase was dried and freed from solvent in vacuo and the residue was fractionated over a column. 332 g (86% of theory) of 2,2-dimethyl-3-oxo-butyl methane-sulphonate of boiling point 106°–120° C./0.12 mm Hg were obtained.

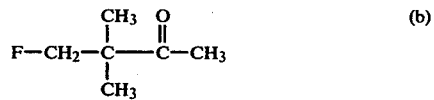

38.8 g (0.2 mol) of 2,2-dimethyl-2-oxobutyl methane-sulphonate were added dropwise to a suspension of 23.2 g (0.4 mol) of dry potassium fluoride in 400 ml of distilled tetraethylene glycol, in a three-necked stirred flask with a descending condenser, at 160° C. and under 20 mbars in the course of 2 hours and the mixture was subsequently stirred for a further 2 hours. The reaction product which had distilled out was condensed in a descending condenser and collected in a subsequent low temperature trap. 20.9 g (89% of theory) of 3,3-dimethyl-4-fluoro-2-butanone of boiling point 130°–134° C. were obtained.

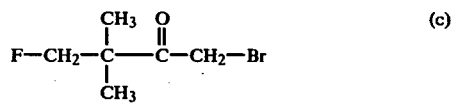

480 g of bromine were slowly added dropwise to a mixture of 354 g (3 mol) of 3,3-dimethyl-4-fluoro-2-butanone and 2,000 ml of ether at 20° C. to 30° C., while cooling and stirring. The yellowish solution was subsequently stirred for a further 1 hour at 20° C. and 500 ml of water were then carefully added. The ether phase was separated off, washed several times with water and dried over sodium sulphate. After distilling off the solvent, the residue was distilled under a waterpump vacuum. 472 g (80% of theory) of 1-bromo-3,3-dimethyl-4-fluoro-2-butanone of boiling point 80°–90° C./11 mm Hg were obtained.

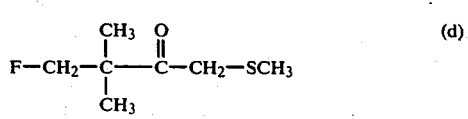

40 g (0.83 mol) of methylmercaptan were passed into 150 ml of methanol at −20° C. A solution of 45 g (0.83 mol) of sodium methylate in 200 ml of methanol was then added dropwise to the same temperature. 154 g (0.78 mol) of 1-bromo-3,3-dimethyl-4-fluoro-butan-2-one were now added dropwise at 0° C. The mixture was stirred for a further 12 hours at 20° C., the inorganic precipitate was filtered off and the filtrate was distilled. 99 g (77% of theory) of 3,3-dimethyl-4-fluoro-1-methylthio-butan-2-one of boiling point 86° C./10 mm Hg were obtained.

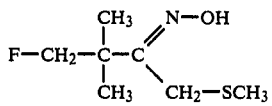
(e)

99 g (0.6 mol) of 3,3-dimethyl-4-fluoro-1-methylthiobutan-2-one, 46 g (0.66 mol) of hydroxylamine hydrochloride and 66.7 g (0.66 mol) of triethylamine in 300 ml of ethanol were heated under reflux for 6 hours. The solvent was then removed in vacuo, the residue was partitioned between methylene chloride and water and the methylene chloride phase was separated off and dried with sodium sulphate. After distilling off the solvent, the residue was distilled in vacuo. 80 g (75% of theory) of 3,3-dimethyl-4-fluoro-1-methylthio-2-hydroximino-butane of boiling point 133° C./13 mm Hg were obtained.

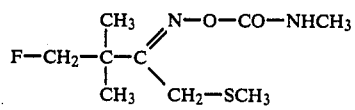
(f)

78 g (0.43 mol) of 3,3-dimethyl-4-fluoro-1-methylthio-hydroxyiminobutane were dissolved in 300 ml of methylene chloride, and 26 g (0.46 mol) of methyl isocyanate were added dropwise. During this addition, the temperature of the reaction solution rose to about 35° C.

After stirring the mixture at room temperature for 5 hours, the solvent was stripped off in vacuo. After triturating the residue with diisopropyl ether, 65 g (64% of theory) of 3,3-dimethyl-4-fluoro-2-methylcarbamoyloximino-1-methylthio-butane were obtained as colorless crystals with a melting point of 50°–53° C.

EXAMPLE 2

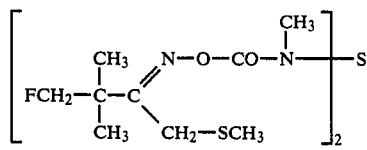
(2)

Process variant (b)

7 g (0.039 mol) of 3,3-dimethyl-4-fluoro-1-methylthio-2-hydroximino-butane and 3.68 g (0.02 mol) of N,N'-bis-(fluorocarbonyl)-thio-bis-methylamine were dissolved together in 100 ml of absolute toluene, and 4 g (0.04 mol) of triethylamine were added dropwise at room temperature. The mixture was stirred at this temperature for a further 24 hours and the toluene phase was washed twice with 50 ml of water each time, dried over sodium sulphate and concentrated. 8 g (80% of theory) of N,N'-bis-(3,3-dimethyl-4-fluoro-1-methylthio-2-oximino-carbonyl-butane)thio-bis-methylamine were obtained as a yellowish, viscous oil.

The following compounds of the general formula

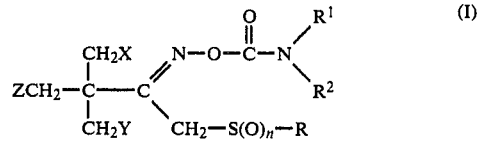
(I)

could be obtained in an analogous manner, and according to process variants (a), (b) and (c):

| Compound No. | X | Y | Z | R | R$^1$ | R$^2$ | n | Melting point (°C.) |
|---|---|---|---|---|---|---|---|---|
| 3 | H | F | F | CH$_3$ | CH$_3$ | H | O | 65 |
| 4 | F | F | F | CH$_3$ | CH$_3$ | H | O | viscous oil |
| 5 | H | H | Cl | CH$_3$ | CH$_3$ | H | O | 25 |
| 6 | H | Cl | Cl | CH$_3$ | CH$_3$ | H | O | viscous oil |
| 7 | H | H | Br | CH$_3$ | CH$_3$ | H | O | viscous oil |
| 8 | H | Br | Br | CH$_3$ | CH$_3$ | H | O | viscous oil |
| 9 | H | F | F | CH$_3$ | CH$_3$ | dimer | O | viscous oil |
| 10 | H | H | Cl | CH$_3$ | CH$_3$ | dimer | O | viscous oil |

The pesticidal activity of the compounds of this invention is illustrated by the following examples wherein the compounds according to the present invention are each identified by the number (given in brackets) from the preparative examples hereinabove:

EXAMPLE 3

Critical concentration test/root-systemic action

Test insect: *Myzus persicae.*
Solvent: 3 parts by weight of acetone.
Emulsifier: 1 part by weight of alkylaryl polyglycol ether.

To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves are infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the following compound showed a superior action compared to the prior art: (1).

EXAMPLE 4

Critical concentration test/root-systemic action

Test insect: Phaedon cochleariae larvae.
Solvent: 3 parts by weight of acetone
Emulsifier: 1 part by weight of alkylaryl polyglycol ether.

To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example the following compound showed a superior action compared to the prior art: (1).

EXAMPLE 5

Phaedon larvae test

Solvent: 3 parts by weight of dimethylformamide.
Emulsifier: 1 part by weight of alkylaryl polyglycol ether.

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into the preparation of the active compound and were infested with mustard beetle larvae (*Phaedon cochleariae*), as long as the leaves were still wet.

After the specified periods of time, the degree of destruction was determined in %: 100% meant that all of the beetle larvae had been killed whereas 0% meant that none of the beetle larvae had been killed.

In this test, for example, the following compound showed a superior activity compared to the prior art: (1).

EXAMPLE 6

Tetranychus test (resistant)

Solvent: 3 parts by weight of dimethylformamide.
Emulsifier: 1 part by weight of alkylaryl polyglycol ether.

To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were treated by being dipped into the preparation of the active compound.

After the specified periods of time, the degree of destruction was determined as a percentage: 100% meant that all of the spider mites were killed whereas 0% meant that none of the spider mites were killed.

In this test, for example, the following compound showed a superior activity compared to the prior art: (1).

It will be appreciated that the instant specification and examples are set forth by way of illustration and not limitation, and that various modifications and changes may be made without departing from the spirit and scope of the present invention.

We claim:

1. A substituted 2-carbamoyloximinobutane of the formula

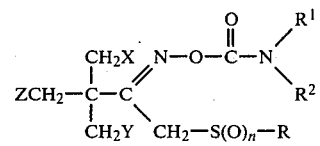

in which
R is alkyl with 1 to 4 carbon atoms or alkylthioalkyl with 1 to 4 carbon atoms in each alkyl moiety,
$R^1$ is alkyl with 1 to 4 carbon atoms, alkoxyalkyl with 1 to 4 carbon atoms in each alkyl moiety, or alkenyl or alkynyl with 2 to 4 carbon atoms,
$R^2$ is hydrogen, alkyl with 1 to 4 carbon atoms or $—SR^3$,
$R^3$ is alkyl with 1 to 4 carbon atoms, halogenoalkyl with 1 to 2 carbon atoms and up to 5 halogen atoms, phenyl, phenyl substituted with halogen, with alkyl with 1 to 2 carbon atoms or with halogenoalkyl with 1 to 2 carbon atoms and up to 5 halogen atoms, alkoxycarbonyl with 1 to 4 carbon atoms in the alkyl moiety, $—N(CH_3)R^4$, or a radical identical to that to which $—SR^3$ is bonded,
$R^4$ is alkyl with 1 to 4 carbon atoms, alkoxycarbonyl with 1 to 4 carbon atoms in the alkyl moiety, or phenylsulphonyl optionally substituted on the phenyl with halogen, with alkyl with 1 to 2 carbon atoms or with halogen-oalkyl with 1 to 2 carbon atoms and up to 5 halogen atoms,
X is hydrogen or halogen,
Y is hydrogen or halogen,
Z is halogen, and
n is 0, 1 or 2.

2. A compound according to claim 1, in which
X is hydrogen, fluorine, chlorine or bromine,
Y is hydrogen, fluorine, chlorine or bromine, and
Z is fluorine, chlorine or bromine.

3. A compound according to claim 1, wherein such compound is 3,3-dimethyl-4-fluoro-2-methylcarbamoyl-oximino-1-methylthio-butane of the formula

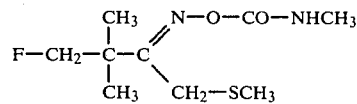

4. A compound according to claim 1, wherein such compound is N,N'-bis-(3,3-dimethyl-4-fluoro-1-methylthio-2-oximino-carbonyl-butane)-thio-bis-methylamine of the formula 5. A compound according to claim 1, wherein such compound is 3,3-dimethyl-4-chloro-2-methylcarbamoyl-oximino-1-methylthio-butane of the formula

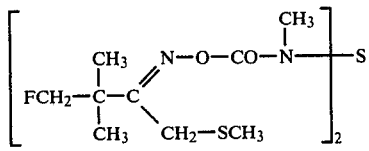

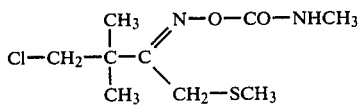

6. An arthropodicidal composition comprising an arthropodicidally effective amount of a compound according to claim 1 in admixture with a diluent.

7. A method of combating arthropods comprising applying to the arthropods, or to a habitat thereof, an arthropodicidally effective amount of a compound according to claim 1.

8. The method according to claim 7, wherein said compound is
3,3-dimethyl-4-fluoro-2-methylcarbamoyl-oximino-1-methylthio-butane,
N,N'-bis-(3,3-dimethyl-4-fluoro-1-methylthio-2-oximino-carbonyl-butane)-thio-bis-methylamine or
3,3-dimethyl-4-chloro-2-methylcarbamoyl-oximino-1-methylthio-butane.

* * * * *